(12) United States Patent
Kagay et al.

(10) Patent No.: US 11,717,071 B2
(45) Date of Patent: Aug. 8, 2023

(54) TANNING METHODS AND ARTICLES THEREFOR

(71) Applicants: Laurel Corrinne Kagay, Austin, TX (US); Mary Rachel George, Austin, TX (US)

(72) Inventors: Laurel Corrinne Kagay, Austin, TX (US); Mary Rachel George, Austin, TX (US)

( * ) Notice: Subject to any disclaimer, the term of this patent is extended or adjusted under 35 U.S.C. 154(b) by 0 days.

(21) Appl. No.: 17/934,128

(22) Filed: Sep. 21, 2022

(65) Prior Publication Data

US 2023/0180915 A1   Jun. 15, 2023

Related U.S. Application Data

(63) Continuation of application No. 16/043,815, filed on Jul. 24, 2018, now abandoned.

(60) Provisional application No. 62/536,794, filed on Jul. 25, 2017.

(51) Int. Cl.
| | |
|---|---|
| *A45D 34/00* | (2006.01) |
| *A45D 34/04* | (2006.01) |
| *A61Q 19/04* | (2006.01) |
| *A61K 8/35* | (2006.01) |
| *A61K 8/60* | (2006.01) |
| *A61Q 19/00* | (2006.01) |
| *A61K 8/00* | (2006.01) |
| *A61Q 17/04* | (2006.01) |
| *A61M 35/00* | (2006.01) |

(52) U.S. Cl.
CPC ............... *A45D 34/04* (2013.01); *A61K 8/00* (2013.01); *A61K 8/35* (2013.01); *A61K 8/60* (2013.01); *A61M 35/25* (2019.05); *A61Q 17/04* (2013.01); *A61Q 19/00* (2013.01); *A61Q 19/04* (2013.01); *A45D 2200/1018* (2013.01); *A45D 2200/25* (2013.01); *A61K 2800/87* (2013.01); *A61K 2800/874* (2013.01); *A61K 2800/882* (2013.01); *A61Q 19/007* (2013.01)

(58) Field of Classification Search
CPC ............ A45D 34/04; A45D 2200/1018; A45D 2200/25; A61K 8/00; A61K 8/35; A61K 8/60; A61K 2800/87; A61K 2800/874; A61K 2800/882; A61M 35/25; A61Q 17/04; A61Q 19/00; A61Q 19/04; A61Q 19/007

USPC ........................................................ 604/290
See application file for complete search history.

(56) References Cited

U.S. PATENT DOCUMENTS

| | | | |
|---|---|---|---|
| 4,466,805 A | 8/1984 | Welters et al. | |
| 4,708,865 A | 11/1987 | Turner | |
| 4,968,497 A | 11/1990 | Wolfram et al. | |
| 5,229,104 A | 7/1993 | Sottery et al. | |
| 5,318,774 A | 6/1994 | Alban et al. | |
| 5,514,437 A | 5/1996 | Tanner et al. | |
| 5,603,923 A | 2/1997 | Robinson et al. | |
| 6,802,830 B1* | 10/2004 | Waters | A45D 34/04 604/289 |
| 2004/0241113 A1 | 12/2004 | Stephens et al. | |
| 2005/0113769 A1* | 5/2005 | Waters | A61M 35/25 604/289 |
| 2011/0270200 A1* | 11/2011 | Edgar | G06V 40/10 604/290 |
| 2013/0142738 A1 | 6/2013 | Turmelle | |
| 2015/0097050 A1* | 4/2015 | Ciervo | B05B 17/0607 239/102.2 |

FOREIGN PATENT DOCUMENTS

GB   2483708 A   *   3/2012   ............. A61Q 19/04

OTHER PUBLICATIONS

The Session, All Natural Sunless Tanning—Chocolate Sun, <https://chocolatesun.com/pages/the-session>, 2 pages, dated 2018.
Best Spray Tan Solution—Spray on Tan—Tanning Solutions—Elite-Tan, E-Tan Mini Roller, <http://elite-tan.com/e-tan-mini-roller/>, 2 pages, retrieved 2019.
Amazon.com: Skinny Tan Roller Applicator Accessories: Beauty, <https://www.amazon.com/Skinny-Tan-Roller-Applicator-Accessories/dp/B06XCNH5CW>, 4 pages, retrieved 2019.
Amazon.com: SUN Laboratories Roll-N-Tan Self Tanning Lotion—Dark 7 fl. oz., <https://www.amazon.com/Laboratories-Roll-N-Tan-Self-Tanning-Lotion/dp/B000VH5GEC>, 5 pages, retrieved 2019.

* cited by examiner

*Primary Examiner* — Eisa B Elhilo
(74) *Attorney, Agent, or Firm* — Abel Schillinger, LLP

(57) ABSTRACT

The present disclosure relates method of tanning a person including applying a moisturizer to an applicator and applying a tanning solution to the applicator. The moisturizer and the tanning solution are applied to the applicator in separate steps. The applicator is then contacted onto the skin of a person to apply the moisturizer and tanning solution.

18 Claims, No Drawings

TANNING METHODS AND ARTICLES THEREFOR

CROSS-REFERENCE TO RELATED APPLICATION

The Application is a continuation of and claims priority under 35 U.S.C. § 120 to U.S. patent application Ser. No. 16/043,815, entitled "TANNING METHODS AND ARTICLES THEREFOR," by Laurel Corrinne Kagay et al., filed Jul. 24, 2018, which claims priority under 35 U.S.C. § 119(e) to U.S. Provisional Patent Application No. 62/536,794, entitled "TANNING METHODS AND ARTICLES THEREFOR," by Laurel Corrinne Kagay et al., filed Jul. 25, 2017, both of which applications are incorporated by reference herein in their entireties for all purposes.

FIELD OF THE DISCLOSURE

The present disclosure relates to methods of tanning the skin of a person, and articles therefor. In particular, tanning is accomplished using a sunless tanning solution.

BACKGROUND

It is widely known that tanning by exposure to the sun's radiation, while effective, has notable health risks. Excessive exposure to the sun can not only cause sunburn, but over time can permanently damage the skin and raise the risk of cancer. Despite those risks, people continue to demand the aesthetic appeal of tanned skin.

Sunless tanning has become increasingly popular as a way to achieve a tanned appearance without the risks associated with tanning by sun exposure (or artificial radiation). One of several chemical compounds is provided in solution and applied to the skin, and reacts with the skin to cause temporary darkening of the skin. Sunless tanning solution is often applied via spray, such as an packaged aerosol, or in the context of a tanning salon, spray booths are often used. In addition, tanning solution may be applied manually by a technician via air brushing. Air brushing is considered by some to be the most natural-looking, aesthetically pleasing tan, mimicking the results from natural tanning via the sun or artificial radiation. However, airbrushing creates a mist that both the customer and the technician breathe in during application, raising health concerns.

One protocol for sunless tanning is described here: https://chocolatesun.com/pages/the-session.

Additional drawbacks associated with spray-based sunless tanning approach include durability, uniformity, color and tone, drying time, skin prep prior to application, and overall feel. Sunless tanning products can often show streaks or blotches, have a non-natural color, have a sticky feel, and can wear off due to sweat or abrasion or the like. As the pigment wears off, sometimes it can come off non-uniformly, creating an even less natural look over the days following treatment.

Other approaches use a tanning lotion, oftentimes having the consistency of skin lotions, which are not suitable for spraying. One product is packaged with an integral roller and can be rolled onto the skin. However, such products tend to perform poorly, with only modest darkening of the skin and unevenness.

A need continues to exist in the industry for improved sunless tanning techniques and products.

DETAILED DESCRIPTION

The following discussion will focus on specific implementations and embodiments of the teachings. The detailed description is provided to assist in describing certain embodiments and should not be interpreted as a limitation on the scope or applicability of the disclosure or teachings. It will be appreciated that other embodiments can be used based on the disclosure and teachings as provided herein.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

According to an aspect, a method of tanning the skin of a person is provided. Here, tanning is carried out by contacting an applicator to the skin. Applicators come in various forms, including sponges, brushes, rollers, etc. An applicator has the functionality to absorb or hold tanning solution and apply the tanning solution to the skin by contact of the applicator to the skin. In one particular aspect, the applicator is a roller. The roller can have a nap, formed of fibers. Fibers can be natural or synthetic and in one embodiment, the fibers are natural mohair. In an embodiment, the roller is sized so as to be easily maneuverable on the skin around and along contours of the body. The roller may be 1" to 9" in length, and in one embodiment, the roller can have a length within a range of 2" to 4.5".

Prior to contact with the skin, the applicator can be exposed to a tanning formulation, or tanning solution, or moisturizer, or a combination thereof. Tanning solutions generally contain an active tanning agent in liquid base. Active tanning agents include Dihydroxyacetone (DHA), which functions to darken at least the outer skin layer of a person through a chemical reaction with the skin, such as by Maillard reaction. Other tanning agents may be used. In addition, the tanning solution may contain other ingredients such as moisturizing species and bronzers. Bronzers can be helpful to track the area of application of the product and the concentration of the product. However, in other embodiments, the tanning solution can be bronzer free.

Moisturizers contain one or several moisturizing species. The moisturizer functions to increase hydration of the skin by reducing evaporation. Moisturizing species include at least one component from the group consisting of skin lipids, skin sterols, oils, humectants, emollients or lubricants. In one embodiment, the moisturizer is free of DHA, and can be free of active tanning agents.

Tanning formulations contain a combination of a tanning agent and a moisturizing species. Tanning formulations may contain a combination of a tanning solution and moisturizer, provided that it contains both a tanning agent and a moisturizing species.

In one particular embodiment, a tanning solution is applied to the applicator, and separately, a moisturizer is applied to the applicator. The moisturizer can be applied first to the applicator, and in the case of a roller, it can partially or full saturate the roller. In the case of first applying the moisturizer, tanning solution is then applied to the roller. Application can be made directly to the roller such as by dispensing product directly onto the roller, or product can be applied to a tray (e.g., paint tray) and the product absorbed into the roller by rolling along a surface of the tray much in the same way paint is applied to a roller in case of painting surfaces. The roller generally includes a roller frame and a roller cover. The roller cover is generally cylindrical and slips onto the roller frame that allows the roller cover to rotate on is longitudinal axis.

Once moisturizer and tanning solution is applied to the applicator, the applicator is brought into contact with skin of a person thereby coating the skin with the combination of tanning solution and moisturizer. During the tanning of a person, the relative proportions of tanning solution and moisturizer can be modified. This can be accomplished by changing the amount of products applied to the roller prior to application to the skin. Changing ratios of tanning solution to moisturizer during tanning can be done to accommodate localized oily, normal or dry areas of the skin. For example, it may be desirable to apply higher concentrations of moisturizer to areas of the skin that are dry, and conversely, lower concentrations of moisturizer to normal to oily areas of skin. The technician applying the products can modify relative proportions of based on observation of product behavior on the skin (e.g., speed of drying) as well as observations of skin condition (dry, normal, oily), for example.

The moisturizer and the tanning solution can be applied separately, such as dispensed from separate containers and onto the applicator. The tanning solution and the moisturizer may be deployed onto the applicator in a range of weight ratios, such as at a weight ratio from 1:1 to 50:1, such as 2:1 to 25:1, such as 2:1 to 15:1.

According to another embodiment, a tanning technique includes contacting an applicator to apply tanning solution and moisturizer to the skin of a person, and contacting a sponge to the skin to blend the applied tanning solution and moisturizer. In this particular embodiment, attention is drawn to use of a sponge to blend the applied products into and/or along the skin of a person. The sponge may be naturally occurring or synthetic and is generally formed of a compressible material that has a network of pores, such as open porosity. The sponge may be hydrophilic, and may be latex free. The sponge can be contacted to the skin by any one of dabbing, rolling, or rubbing to smooth out non-uniform pigmented areas on the skin. The sponge may be pre-wetted with water such that the sponge is damp upon application to the skin.

According to a particular feature, the application of the sponge advantageously smooths out the pigmentation of the tanning solution to help create a smooth, uniform color tone with minimized streaks, blotches or other areas of hyper- or hypo-pigmentation. Further refinement of coloring or pigmentation of the skin can be accomplished with following up application of damp sponge with a second sponge by any one of dabbing, rolling, or rubbing to smooth out non-uniform pigmented areas on the skin. The second sponge may be dry, such as having a moisture content of ambient or lesser moisture content such in the case of a sponge sealed in a package at a set relative humidity.

According to another aspect, localized areas of the skin may be pre-treated with moisturizer prior to contacting the applicator to the skin. Pre-treatment can be carried out on various areas of the body, notably the feet, elbows, knees, or hands of the person. Pre-treatment can help prevent unwanted, hyper-pigmentation of dry areas of the skin.

In one aspect, multiple applications of the moisturizer and tanning solution can applied to localized areas to promote a natural appearance similar to what is often observed from sun tanning. Localized areas may include the shoulders, shins, or chest area of the person. In one development, multiple applications of the moisturizer and tanning solution are applied to localized areas to create a shadowing effect to promote a 3-dimensional appearance to the localized body part. This shadowing or 3-dimensional effect can be used to enhance the appearance of muscularity or muscle definition, and may be useful for competitors participating in body-building, figure, fitness shows, or the like. Localized areas may include, for example, jawline, cheeks, biceps, triceps, pectorals, abs, calves, hips, hamstrings, or cleavage.

Certain aspects call for disposition of tanning solution and moisturizer separately onto an applicator, such as a roller. The tanning solution and moisturizer can be packaged separately, and independent disposition of products allows modification of tanning solution to moisturizer ratio depending on the body part undergoing exposure, and/or depending on the skin condition of a particular client. The ratio of components can be changed based on dryness of the skin, with dry skin requiring higher concentrations of moisturizer relative to tanning solution, and oily skin requiring lower concentrations of moisturizer relative to tanning solution. The relative amounts of moisturizer and tanning solution can be adjusted during the tanning process to permit adequate working time (to prevent drying of the products) yet at the same time providing adequate tanning of the localized skin area.

In addition to methods for tanning skin, a tanning toolkit can be provided containing tools for carrying out tanning. Such a toolkit can be packaged together, and can include a roller, a moisturizer, a tanning solution, a tray for dispensing and holding the products, and a sponge.

In yet another aspect, tanning solution and moisturizer are not provided separately, but instead a tanning formulation is provided that contains both a tanning agent and a moisturizing species. Here, multiple tanning formulations are provided, such as in the form of a kit, having either varying levels of moisturizing species or varying species of moisturizer, or both. For example, a range of formulations may be separately packaged for disposition on an applicator, with formulations designed for dry, normal, and oily skin, for example, each formulation having a different moisturizing properties. In one embodiment, the formulations are similar, varying mainly in the quantity of moisturizing species relative to tanning solution.

In the case of provision of a range of tanning formulations, generally at least first and second formulations are provided, the first and second formulations having different concentrations of moisturizing species and/or different moisturizing species. In one development, the first tanning formulation has a higher concentration of moisturizing species than the second tanning formulation, and at least initially during the tanning process, the first tanning formulation is applied to the skin of the person.

Many different aspects and embodiments are possible. Some of those aspects and embodiments are described herein. After reading this specification, skilled artisans will appreciate that those aspects and embodiments are only illustrative and do not limit the scope of the present invention. Embodiments may be in accordance with any one or more of the embodiments as listed below.

Examples

The concepts described herein will be further described in the following Examples, which do not limit the scope of the invention described in the claims.

Example

The knees, elbows, hands and feet of a client were pre-treated with Epionce Renewal Enriched Body Lotion moisturizer. A 4" mohair roller is provided with matching tray, generally commercially available from paint or hardware stores. Epionce Renewal Enriched Body Lotion moisturizer is dispensed onto the nap of the roller, along its entire length, and the moisturizer is worked into the nap by rolling along the tray. Separately, Revelation High Definition Rapid Tan Solution (produced by Biddiscombe Sunless) is applied to the roller and the product worked into the roller. The roller is applied to the back of the leg of the client, covering approximately the entire length of the calf and about one third to one half the circumference of the calf. Immediately after application a moistened Body Blender (available from BeautyBlender.com or Rea.deeming, Inc.) is lightly brushed over the applied area to smooth out the products and to soften the edges of the application site, followed by a dry Body Blender sponge in select areas. Additional tanning solution is applied to the roller by rolling the roller into accumulated product in the tray and application continues along a localized area adjacent the first application site. Blending is carried out as above, using a wet then dry Body Blender sponges. The process is continued, with additional moisturizer being applied as needed, especially when approaching skin areas that are relatively dry. Extra passes of the applicator were done along the chest and shoulders for extra pigmentation along these area.

14 g of moisturizer and 61 g of tanning solution were dispensed onto the roller, approximately a 4:1 ratio of tanning solution to moisturizer. It is noted that some product was left over in the tray and absorbed into the nap. The client undergoing treatment had overall dry skin.

Application to the entire body took 35 minutes, and the result was a very uniform, appealing color and tone. As the tan faded over the next week to 10 days, the changes in color were gradual and subtle, with limited blotches or localized area of peeling.

The following Items describe other aspects.

Embodiment 1. A method of tanning a person, comprising: applying a moisturizer to an applicator; applying a tanning solution to the applicator, wherein the moisturizer and the tanning solution are applied to the applicator in separate steps; contacting the applicator onto the skin of a person to apply the moisturizer and tanning solution.

Embodiment 2. The method of embodiment 1, further comprising: contacting a sponge to the skin to blend the applied tanning solution and moisturizer.

Embodiment 3. The method of embodiment 2, wherein the sponge is contacted against the skin by any one of dabbing, rolling, or rubbing to smooth out non-uniform pigmented areas on the skin.

Embodiment 4. The method of embodiment 2, wherein the sponge is hydrophilic, and wherein the sponge is latex-free.

Embodiment 5. The method of embodiment 2, wherein the sponge is moistened prior to contacting the skin.

Embodiment 6. The method of embodiment 5, wherein further comprising the step of applying a second sponge to the skin after applying the first sponge, the second sponge being dry.

Embodiment 7. The method of any of the preceding embodiments, wherein the applicator comprises a roller.

Embodiment 8. The method of embodiment 7, wherein the roller comprises natural hair fibers, such as mohair.

Embodiment 9. The method of any of the preceding embodiments, wherein the tanning solution and the moisturizer are applied to the applicator at a weight ratio from 1:1 to 50:1, such as 2:1 to 25:1, such as 2:1 to 15:1.

Embodiment 10. The method of any of the preceding embodiments, wherein the moisturizer is water-based.

Embodiment 11. The method of embodiment 10, wherein the moisturizer functions to increase hydration of the skin by reducing evaporation, containing at least one component from the group consisting of: skin lipids, skin sterols, oils, humectants, emollients or lubricants.

Embodiment 12. The method of any of the preceding embodiments, wherein the tanning solution comprises a tanning agent that chemically reacts with the skin to cause pigmentation to darken skin tone.

Embodiment 13. The method of embodiment 12, wherein the tanning solution contains at least one of DHA (Dihydroxyacetone) or erythrulose.

Embodiment 14. The method of embodiment 13, wherein the DHA is present in the tanning solution within a range of 0.5 to 20 wt %, such as 5 to 20 wt %, or such as 5 to 15 wt %.

Embodiment 15. The method of any of the preceding embodiments, further comprising a step of pre-treating localized areas of the skin with moisturizer prior to contacting the applicator to the skin.

Embodiment 16. The method of embodiment 15, wherein pre-treating includes applying moisturizer to any of the elbows, knees, hands, or feet of the person.

Embodiment 17. The method of any one of the preceding embodiments, wherein multiple applications of the moisturizer and tanning solution are applied to the shoulders, shins, or chest area of the person.

Embodiment 18. The method of any one of the preceding embodiments, wherein multiple applications of the moisturizer and tanning solution are applied in localized body parts to create a shadowing effect to promote a 3-dimensional appearance to the localized body part.

Embodiment 19. The method of embodiment 18, wherein the localized body part includes at least one part from the group consisting of: jawline, cheeks, biceps, triceps, pectorals, abs, calves, hips, hamstrings, or cleavage.

Embodiment 20. A method of tanning a person, comprising: applying a first tanning formulation to the skin of a person, the first tanning formulation comprising a first tanning agent and a first moisturizing species present in the first tanning formulation at a first concentration; and applying a second tanning formulation to the skin of a person, the second tanning formulation comprising a second tanning agent and a second moisturizing species present in the second tanning formulation at a second concentration, wherein at least one of (i) the first and second concentrations are different, and (ii) the first and second moisturizing species are different.

Embodiment 21. The method of embodiment 20, wherein the first and second tanning formulations are applied on different areas of the skin of the person.

Embodiment 22. The method of embodiment 20, wherein the first concentration is higher than the second concentration.

Embodiment 23. The method of embodiment 20, wherein the first tanning formulation is applied prior to the second tanning formulation.

Embodiment 24. A tanning toolkit, comprising: a roller; a tray; tanning solution; moisturizer, wherein the tanning solution and the moisturizer are separately packaged; and a sponge.

Embodiment 25. A tanning toolkit, comprising: a first tanning formulation comprising a first tanning agent and a first moisturizer present in the first tanning formulation at a first concentration; and a second tanning formulation comprising a second tanning agent and a second moisturizer present in the second tanning formulation at a second concentration, wherein at least one of (i) the first and second concentrations are different, and (ii) the first and second moisturizing species are different; and an applicator for applying at least one of the first or second tanning solutions to the skin of a person.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:

1. A method of tanning a person, comprising:
applying a moisturizer to an applicator;
applying a tanning solution to the applicator, wherein the moisturizer and the tanning solution are applied to the applicator in separate steps;
contacting the applicator onto the skin of a person to apply the moisturizer and tanning solution, wherein the tanning solution and the moisturizer are applied to the applicator at a weight ratio from 1:1 to 50:1.

2. A method of tanning a person, comprising:
applying a moisturizer to an applicator;
applying a tanning solution to the applicator, wherein the moisturizer and the tanning solution are applied to the applicator in separate steps;
contacting the applicator onto the skin of a person to apply the moisturizer and tanning solution;
contacting a sponge to the skin to blend the applied tanning solution and moisturizer,
wherein the sponge is contacted against the skin by any one of dabbing, rolling, or rubbing to smooth out non-uniform pigmented areas on the skin.

3. The method of claim 2, wherein the sponge is hydrophilic, and wherein the sponge is latex-free.

4. The method of claim 2, wherein the sponge is moistened prior to contacting the skin.

5. The method of claim 4, wherein further comprising the step of applying a second sponge to the skin after applying the first sponge, the second sponge being dry.

6. The method of claim 1, wherein the applicator comprises a roller.

7. The method of claim 6, wherein the roller comprises natural hair fibers.

8. The method of claim 7, wherein the natural fibers comprise mohair.

9. The method of claim 1, wherein the moisturizer is water-based.

10. The method of claim 9, wherein the moisturizer functions to increase hydration of the skin by reducing evaporation, containing at least one component from the group consisting of skin lipids, skin sterols, oils, humectants, emollients or lubricants.

11. The method claim 1, wherein the tanning solution comprises a tanning agent that chemically reacts with the skin to cause pigmentation to darken skin tone.

12. The method of claim 11, wherein the tanning solution contains at least one of DHA (Dihydroxyacetone) or erythrulose.

13. The method of claim 12, wherein the DHA is present in the tanning solution within a range of 0.5 to 20 wt %.

14. A method of tanning a person, comprising:
applying a moisturizer to an applicator;
applying a tanning solution to the applicator, wherein the moisturizer and the tanning solution are applied to the applicator in separate steps;
contacting the applicator onto the skin of a person to apply the moisturizer and tanning solution;
pre-treating localized areas of the skin with moisturizer prior to contacting the applicator to the skin.

15. The method of claim 14, wherein pre-treating includes applying moisturizer to any of the elbows, knees, hands, or feet of the person.

16. A method of tanning a person, comprising:
applying a moisturizer to an applicator;
applying a tanning solution to the applicator, wherein the moisturizer and the tanning solution are applied to the applicator in separate steps;
contacting the applicator onto the skin of a person to apply the moisturizer and tanning solution;
wherein multiple applications of the moisturizer and tanning solution are applied to the shoulders, shins, or chest area of the person.

17. The method of claim 1, wherein multiple applications of the moisturizer and tanning solution are applied in localized body parts to create a shadowing effect to promote a 3-dimensional appearance to the localized body part.

18. The method of claim 17, wherein the localized body part includes at least one part from the group consisting of: jawline, cheeks, biceps, triceps, pectorals, abs, calves, hips, hamstrings, or cleavage.

\* \* \* \* \*